United States Patent [19]

Kayser

[11] Patent Number: 5,226,893
[45] Date of Patent: Jul. 13, 1993

[54] HYPODERMIC SYRINGE

[76] Inventor: Edward R. J. Kayser, "Lyndhurst" Wellington Road, Wandin, Victoria 3139, Australia

[21] Appl. No.: 663,918

[22] PCT Filed: Jul. 9, 1990

[86] PCT No.: PCT/AU90/00295
§ 371 Date: May 8, 1991
§ 102(e) Date: May 8, 1991

[87] PCT Pub. No.: WO91/00747
PCT Pub. Date: Jan. 24, 1991

[30] Foreign Application Priority Data
Jul. 12, 1989 [AU] Australia ............... PJ5195

[51] Int. Cl.$^5$ ............................................. A61M 5/32
[52] U.S. Cl. ..................... 604/195; 604/110; 604/171; 604/196; 604/197
[58] Field of Search ............... 604/110, 117, 162, 167, 604/195, 196, 197, 198, 171, 240, 263

[56] References Cited

U.S. PATENT DOCUMENTS

| | | | |
|---|---|---|---|
| 3,066,671 | 12/1962 | Cohen | 604/195 |
| 3,587,575 | 6/1971 | Lichtenstein | 604/195 |
| 4,909,793 | 3/1990 | Vining et al. | 604/197 |
| 4,917,669 | 4/1990 | Bonaldo | 604/198 |
| 4,936,830 | 6/1990 | Verlin | 604/198 |
| 4,938,745 | 7/1990 | Sagstetter | 604/198 |
| 4,950,252 | 8/1990 | Luther et al. | 604/198 |

FOREIGN PATENT DOCUMENTS

| | | |
|---|---|---|
| 1259388 | 9/1988 | Australia . |
| 1308888 | 9/1988 | Australia . |
| 1418988 | 10/1988 | Australia . |
| 1536688 | 11/1988 | Australia . |
| 1623488 | 12/1988 | Australia . |
| 8904681 | 6/1989 | World Int. Prop. O. . |

Primary Examiner—C. Fred Rosenbaum
Assistant Examiner—Ronald K. Stright, Jr.
Attorney, Agent, or Firm—William H. Murray; Frank M. Linguiti

[57] ABSTRACT

A hypodermic syringe includes an elongate housing having rear and forward ends and a piston chamber which slidably supports the piston to define an innoculant storage space within the housing, a hollow needle supported by the plunger assembly and in communication with the storage space. The needle is extendable from the forward end of the housing and retractable into the housing during an injection stroke and a safety device is provided for preventing re-use of the syringe after completion of the injection stroke. The safety device includes an override chamber at the rear end of the housing and adjoining the piston chamber, the override chamber having a greater width than the piston chamber, and a displaceable diaphragm located at or adjacent the juncture of the piston and the override chambers to partition and seal the override chamber from the piston chamber, the diaphragm being displaced by the piston and the piston entering the override chamber at the end of the injection stroke.

12 Claims, 3 Drawing Sheets

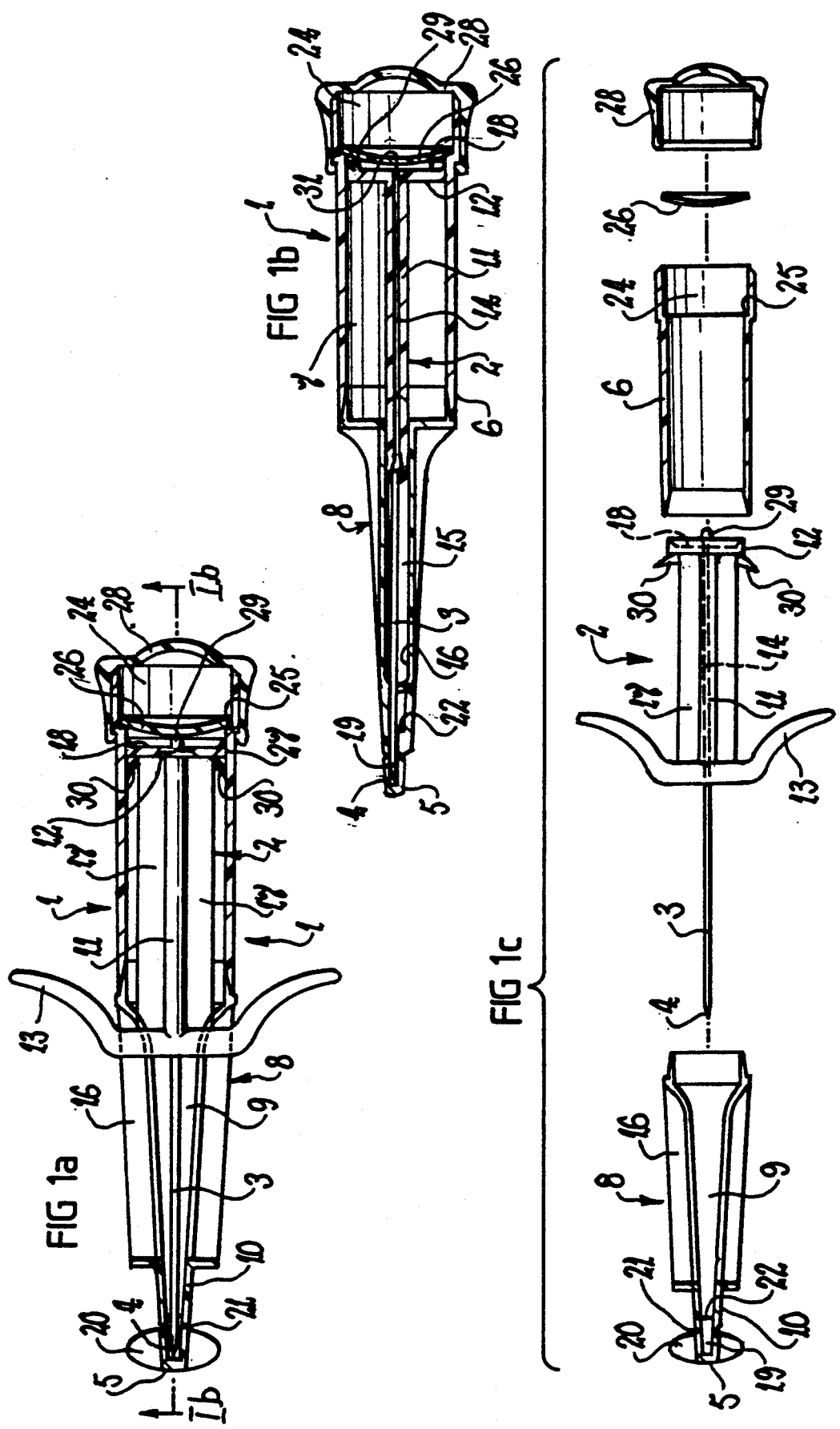

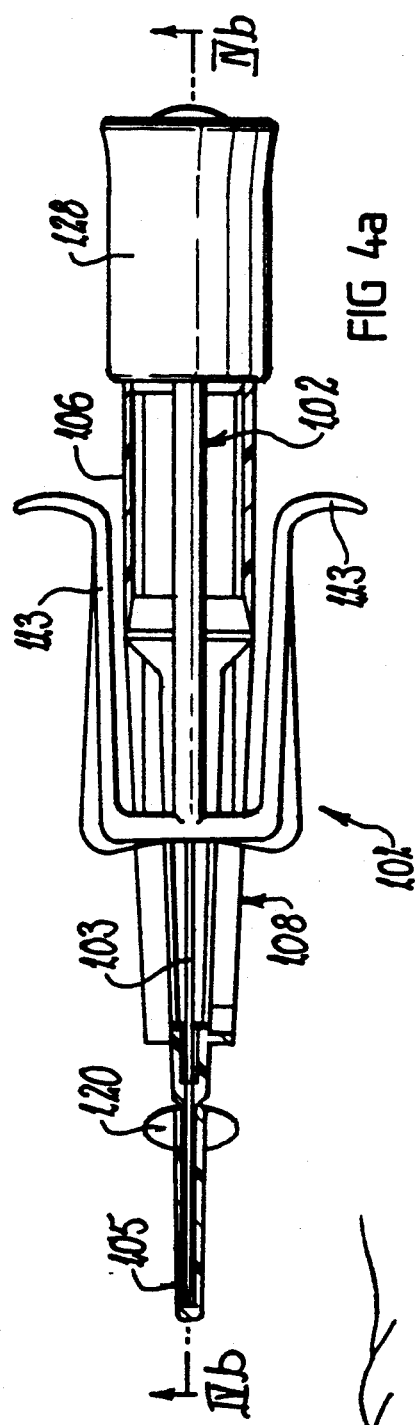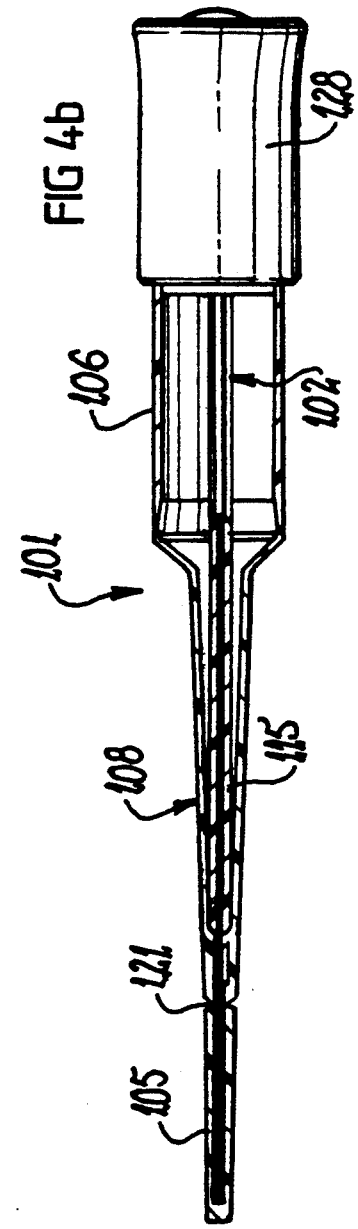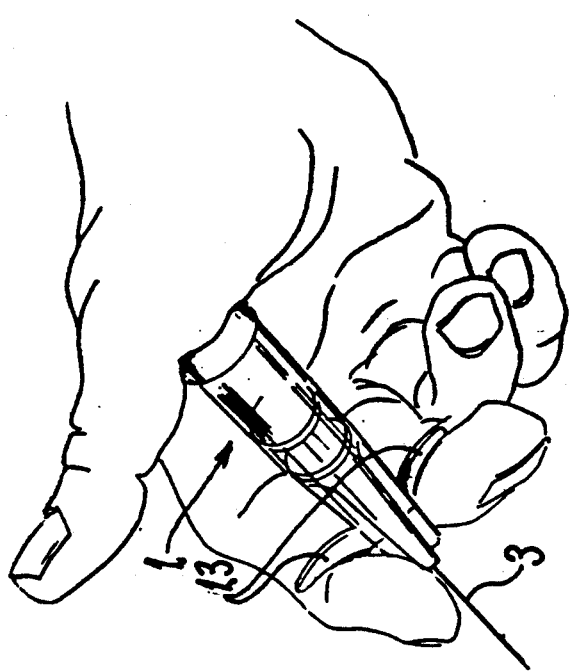

HYPODERMIC SYRINGE

FIELD OF THE INVENTION

This invention relates to a hypodermic syringe, and in particular to a hypodermic syringe having a retractable needle. This invention is applicable for medical and veterinary applications, and it will be convenient to hereinafter describe the invention in relation to that exemplary application. However, it is to be appreciated that the invention is not limited to those applications.

DESCRIPTION OF THE RELATED ART

Following the international concern on the spread of the A.I.D.S. virus, it is now realised that one major form of transmission of this virus is through contact with or use of syringes that have been infected with the A.I.D.S. virus.

In conventional hypodermic syringes, the needle remains exposed after use of that syringe. There is therefore the possibility of being accidentally pricked by the needle after the syringe has been used. This may result in infection with the A.I.D.S. virus if the patient is a carrier of that virus. Furthermore, the disposal of used syringes can be a hazardous procedure because of the exposed needles and the possibility that any one of the syringes may be infected.

Another disadvantage of conventional hypodermic syringes is that the syringe can be readily re-used. In the case of intravenous drug users, a single syringe is often shared by a number of people. This greatly increases the possibility of contracting the A.I.D.S. virus. If one of the persons is a carrier of the virus and infects the syringe, this syringe will infect the others with the virus.

Syringes have been developed where the needle can be retracted after the syringe has been used. Examples of such syringes are disclosed in Australian Patent Application Nos. 13088/88, 14189/88 and 16234/88. These prior syringes are generally arranged in the same way as conventional syringes with a hollow needle extending from one end of a cylindrical housing and a plunger assembly extending from the other end of the housing for displacing a piston supported therein. Means may be provided on the piston to engage an end of the needle at the end of the injection stroke. The needle can then be withdrawn by pulling the piston back through the housing. Alternatively, the needle is supported on means which allow the needle to be withdrawn after the injection stroke.

In these prior arrangements, the needle remains exposed at the end of the injection until the retracting means are actuated. There is therefore still a possibility of accidental contact with the needle immediately after the syringe has been used. Also, because the plunger assembly must be pulled back after the injection or the needle support must be actuated to retract the needle, the user may neglect to or have insufficient time to retract the needle so that it remains exposed after syringe use thereby negating the benefit of the retracting means.

It is therefore an object of the present invention to provide a hypodermic syringe having a hypodermic needle which can be retracted during the injection stroke of the syringe to minimise the possibility of accidental contact with the needle.

It is also a preferred object of the present invention to provide a single use hypodermic syringe which cannot be or is difficult to re-use.

SUMMARY OF THE INVENTION

With this in mind, the present invention provides a hypodermic syringe for the injection of an inoculant liquid including a housing, a plunger assembly slidably supported by the housing, and a hollow needle which can be fully accommodated within and be extendible from the housing wherein the needle is supported by the plunger assembly and retracts into the housing during an injection stroke of the syringe.

As the needle retracts into the housing during the injection stroke, there is no need for a further actuation of the syringe to retract the needle.

The hypodermic syringe preferably further includes safety means for trapping the needle within the housing after the completion of the injection stroke. The plunger assembly preferably includes an elongate stem having a piston at one end thereof, the needle extending from the opposing end thereof and having a longitudinal needle passage in communication with a longitudinal stem passage passing completely through the stem and the piston.

The housing preferably includes an elongate main body portion having a cylindrical chamber therein for slidably supporting the piston, an elongate safety shroud portion having a forward tip and a needle chamber therein for accommodating the needle, and a needle bore passing through the forward tip of the safety shroud portion from the needle chamber.

The safety means previously referred to may include a shoulder provided adjacent the needle bore and within the needle chamber for trapping the tip of the needle when the needle is completely withdrawn from the needle bore into the needle chamber, the needle moving out of alignment with the needle bore when not constrained therein. The longitudinal axis of the needle may be offset at an angle from the longitudinal axis of the stem when the needle is not constrained.

The safety means also or alternatively include an override chamber within the main body portion at a terminal end of the housing, the override chamber adjoining and having a greater width than the diameter of the cylindrical chamber for accommodating the piston after the completion of the injection. A displaceable diaphragm may be provided at or adjacent the juncture of the cylindrical and override chambers for partitioning and sealing the override chamber from the cylindrical chamber, the diaphragm being displaced by the piston as it enters the override chamber. The diaphragm may have an interference fit within the override chamber, a shallow undercut being preferably provided in the wall of the override chamber to assist in locating and holding the diaphragm in position. The piston may also have a projection extending therefrom and towards the diaphragm, the projection being located adjacent to or near the periphery of the piston and being used to facilitate the dislodgment of the diaphragm.

At least one outwardly extending barb may also be provided adjacent the piston for preventing movement of the piston back into the cylindrical chamber after the piston enters the override chamber.

A needle cap may be integrally formed with and separable from the forward tip of the safety shroud portion, the forward tip having a frangible weakened portion adjacent to the needle cap whereby the needle cap can be twisted and separated from the forward tip to expose the portion of the needle held therein.

The plunger assembly preferably includes at least one handle member extending laterally from the stem at or adjacent the opposing end thereof, an elongate longitudinal slot being provided in the housing to allow the or each handle member to extend out from the housing. A peripheral wall preferably extends along at least a substantial portion of the periphery of the or each longitudinal slot.

The following description refers in more detail to the various features of the hypodermic syringe of the present invention. To facilitate an understanding of the invention, reference is made in the description to the accompanying drawings where the hypodermic syringe is illustrated in preferred embodiments. It is to be understood that the hypodermic syringe of the present invention is not limited to the preferred embodiments as illustrated in the drawings.

BRIEF DESCRIPTION OF THE DRAWINGS

FIG. 1A is a longitudinal cross-sectional view of a first preferred embodiment of the hypodermic syringe of the present invention;

FIG. 1B is a longitudinal cross-sectional view taken through Section 1B of FIG. 1A;

FIG. 1C is an exploded view of the hypodermic needle of FIGS. 1A and 1B;

FIG. 3 is a perspective view of the hypodermic syringe of FIGS. 1A and 1B showing a preferred way to hold the syringe during the injection;

FIG. 4A is a longitudinal partial cross-sectional view of a second preferred embodiment of the hypodermic syringe of the present invention; and FIG. 4B is a longitudinal view taken through Section 4B of FIG. 4A.

Referring initially to FIGS. 1A to 3, there is shown a first preferred embodiment of the hypodermic syringe of the present invention. The hypodermic syringe includes a housing 1, a plunger assembly 2 slidably supported within housing 1, and a hypodermic or hollow needle 3 integral with an extending from plunger assembly 2. Plunger assembly 2 and needle 3 move together as a single assembly. FIGS. 1A and 1B show the hypodermic syringe as supplied prior to use with needle 3 retracted within housing 1. It is also envisaged that the syringe be supplied with needle 3 extended and with the syringe preloaded with inoculant liquid.

Figure 2A:
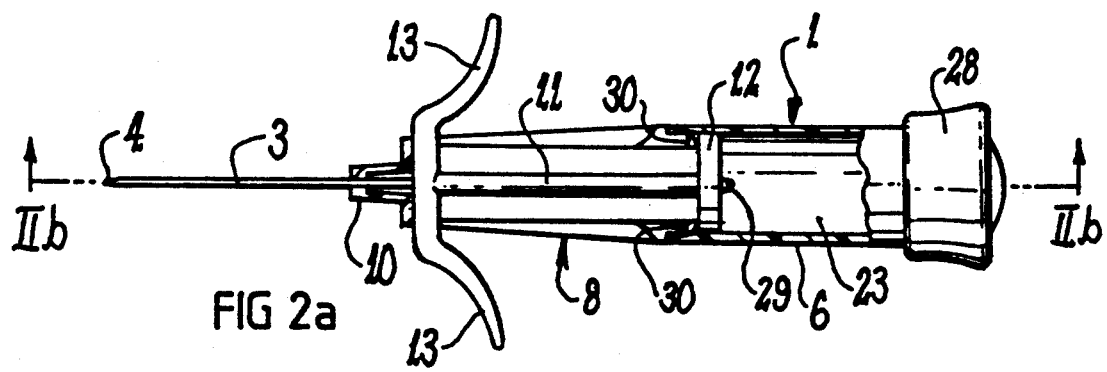
FIG. 2A is a longitudinal cross-sectional view of the hypodermic syringe of FIGS. 1A and 1B showing the needle fully extended prior to injection.
Figure 2B:
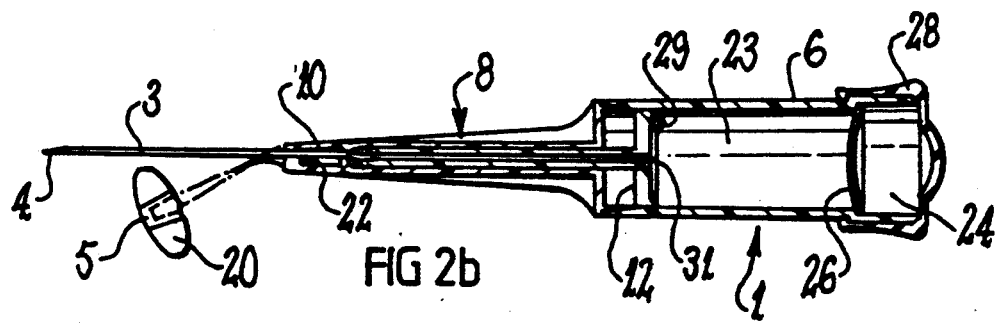
FIG. 2B is a longitudinal cross-sectional view taken through Section 2B of FIG. 2A.

Housing 1 may be elongate and may have a main body portion 6 providing an elongate chamber 7 therein. The lateral cross-section of chamber 7 may be circular to provide a cylindrical chamber. Non-circular lateral cross-sections for chamber 7 are also envisaged. From one end of main body portion 6 extends a safety shroud 8 having a needle chamber 9 therein for accommodating needle 3. Cylindrical chamber 7 and needle chamber 9 are in communication to provide a single elongate and continuous chamber for accommodating the integral plunger assembly 2 and needle 3. Safety shroud 8 and main body portion 6 are joined together to provide elongate housing 1 of the syringe. In a preferred form, main body portion 6 may be substantially cylindrical in shape with safety shroud 8 being tapered to provide a forward tip 10 of housing 1. Needle 3 extends from forward tip 10 when the syringe is used.

Plunger assembly 2 may have an elongate stem 11, a piston 12 at one end of stem 11 and a handle means 13 at or near the opposing end of stem 11. The longitudinal axis of stem 11 is preferably at least substantially parallel to the longitudinal axis of housing 1 when plunger assembly 2 is supported by housing 1. These longitudinal axes may also be substantially aligned. Needle 3 preferably extends from the opposing end of stem 11. The longitudinal axis of needle 3 and stem 11 may be at least substantially aligned when the syringe is in use. Alternatively longitudinal axis of needle 3 may be offset at an angle to the longitudinal axis of stem 11. A longitudinal stem passage 14 passing completely through stem 11 may be provided. Hypodermic needle 3 has a longitudinal passage passing completely therethrough to allow passage of inoculant liquid. Stem passage 14 may be in communication with the longitudinal needle passage to thereby provide a continuous passage through stem 11 and needle 3.

Handle means 13 may include at least one member extending at least substantially laterally from stem 11 relative to its longitudinal axis. Preferably two such handle members 13 are provided extending laterally in opposing directions from stem 11. Each handle member 13 may for example be a simple lateral arm or may have a curved and flattened shape to provide finger rests as shown in the drawings. Handle member 13 may alternatively have an aperture to allow a finger to be passed therethrough.

A longitudinal slot 15 may be provided in the wall of safety shroud 8 for each handle member 13 to enable handle members 13 to extend externally from housing 1. This enables the longitudinal displacement of plunger assembly 2 and needle 3 to be controlled from outside the syringe housing 1. The length of slot 15 may be sufficient to allow needle 3 to be fully extended or fully contracted, the handle members 13 preferably abutting the peripheral ends of slot 15 at either of the above needle positions. A peripheral wall 16 may extend along at least a substantial portion of the periphery of each slot 15. The provision of wall 16 makes it more difficult to manipulate needle 3 when it is fully retracted within safety shroud 8. To make the syringe even more tamper resistant, handle members 13 may be formed with a relatively thin section so that slot 15 can be made very narrow thereby restricting access to needle 3. To ensure that the thinner handle members 13 are of sufficient strength, they may be made of a high strength, low weight material such as magnesium metal. The complete plunger assembly 2 may be made of this material.

Reinforcement means may be provided on stem 11 to increase its rigidity so as to prevent bending of stem 11 during use of the syringe. The reinforcement means may also assist in guiding plunger assembly 2 within housing 1.

The reinforcement means may for example include at least one web 17 extending from stem 11. Each web 17 may extend laterally from stem 11 and longitudinally therealong. Preferably four of these webs 17 can extend equidistantly about stem 11 such that each web 17 is displaced 90° about stem 11 from an adjacent web 11. Alternatively, just two opposing webs 17 may be provided as shown in the drawings. Web(s) 17 may preferably be integrally joined to handle members 13, stem 11 and piston 12 to ensure that plunger assembly 2 moves as a single unit and to prevent or minimise deflection of stem 11, handle members 13 or piston 12 from their correct operating positions.

Piston 12 may be slidably accommodated within, cylindrical chamber 7 and in sealing engagement with the wall of that chamber 7. Piston 12 may have a piston face 18 extending at least substantially laterally relative to the longitudinal axis of stem 11 with stem passage 14 having an inlet/outlet opening 31 in piston face 18. Cylindrical chamber 7 may have a terminal end opposing piston 12 which is preferably closed off so that cylindrical chamber 7 and piston 12 can define a liquid holding space 23 (as shown in FIGS. 2A and B) in which the inoculant liquid to be injected can be held prior to injection. The terminal end may be provided by an end wall closing off cylindrical chamber 7 or may be provided by a displaceable sealing diaphragm 26 as shown in the drawings. Liquid holding space 23 may therefore be defined by cylindrical chamber 7, piston face 18 and diaphragm 26.

Needle 3, when fully retracted, can be accommodated within needle chamber 9 of safety shroud 8. A needle bore 19 may extend from needle chamber 9 through forward tip 10 of housing 1 to allow needle 3 to extend out of housing 1. Needle 3 may be extended by forwardly displacing the handle member(s) 13 towards forward tip 10 of housing 1 to the position as illustrated in FIGS. 2A and B. This will displace plunger assembly 2 towards forward tip 10, resulting in needle 3 extending through needle bore 19 and out of housing 1. The forward movement of plunger assembly 2 also displaces piston 12 away from diaphragm 26 thereby increasing the volume of liquid holding space 23. To retract needle 3, handle members 13 are rearwardly displaced away from forward tip 10 which results in the displacement of plunger assembly 2 away from forward tip 10 retracts needle 3 back into safety shroud 8 and displaces piston 12 towards diaphragm 26 reducing the volume of liquid storage space 23.

Prior to use of the syringe, needle tip 4 may be accommodated within needle bore 19 in forward tip 10. Needle bore 19 may terminate within a separate needle cap 5 which may be releasably secured to forward tip 10. Alternatively, needle cap 5 may be formed as an integral part of safety shroud 8 as shown in the illustrated embodiment. Forward tip 10 may be provided with opposing twist tabs 20 extending laterally therefrom. It is also envisaged that a plurality of ribs be provided on the outer surface of needle cap 5 to enable it to be securely gripped by the fingers. A weakened frangible area may be provided in forward tip 10 adjacent twist tabs 20. This may simply be provided by an annular groove 21 encircling forward tip 10.

Using twist tabs 20, needle cap 5 can be twisted off forward tip 10 to expose needle tip 4, needle cap 5 breaking away from the remainder of forward tip 10 at annular groove 21. This arrangement helps to prevent contamination of needle 3 prior to the actual use of the syringe. It also provides a visual indication that the syringe has been used or otherwise tampered with.

It is also envisaged that a nozzle seal may simply be provided to cover the exit opening of needle bore 19. The seal may preferably be formed integrally with forward tip 10. Needle tip 4 must initially break through the seal before the syringe can be used. The seal should therefore be relatively thin to allow it to be pierced by the needle. To break through the seal, plunger assembly 2 must be forwardly displaced so that needle 3 can penetrate through the seal.

After a small portion of needle 3 is exposed with the removal of needle cap 5, the needle tip 4 may be inserted into a bottle of inoculant liquid for drawing the required dose. As needle 3 is extended further from housing 1, the volume of liquid storage space 23 within the syringe increases inducing a vacuum which can draw the inoculant liquid up through needle 3 and through stem passage 14 to storage space 23. Needle 3 may be extended until the syringe is fully charged with liquid or when the correct dosage of liquid is held therein.

The liquid may then be injected by displacing housing 1 towards the point of penetration of needle 3. This may be accomplished with one hand as shown in FIG. 3 by engaging one or more fingers with the handle members 13 extending from housing 1 and resting the palm or the thumb of the hand on the rear end of housing 1. By pressing the rear end of housing 1 with the palm or thumb towards handle members 13, liquid storage space 23 is made to decrease in volume thereby forcing the liquid out through stem passage 14 and needle 3 to the injection area. During the injection stroke, needle 3 is progressively retracted back into housing 1.

Needle 1 preferably retracts completely into housing 1 at the end of the injection and safety means may be provided to prevent or make it difficult for the syringe to be used again. This safety means may include a shoulder 22 immediately adjacent to needle bore 19. Shoulder 22 may form the forward end of needle chamber 9 behind needle bore 19. Whereas needle bore 19 preferably has a diameter which provides minimal clearance between bore 19 and needle 3 when held therein, needle chamber 9 is relatively wider than bore 19 so that shoulder 22 is provided behind needle bore 19.

Needle tip 4 can be trapped by shoulder 22 when needle 3 is fully retracted within needle chamber 9. To facilitate the trapping of needle tip 4, needle 3 may move out of alignment with needle bore 19 when not constrained therein.

In one arrangement, needle 3 may be provided with an "offset bias" wherein the longitudinal axis of needle 3 normally deviates at an angle from the longitudinal axis of stem 11 when needle 3 is not constrained. The bias angle may be relatively small e.g. about 1.0 degrees. When plunger assembly 2 is supported within cylindrical chamber 7, the longitudinal axis of stem 11 may be parallel to and aligned with the longitudinal axis of needle bore 19 before and during use of the syringe. As needle 3 is supported by and constrained by needle bore 19, the longitudinal axis of needle 3 is initially aligned with the longitudinal axis of needle bore 19. Needle 3 is therefore deflected against its offset bias resulting in a spring tension being maintained in needle 3 before and during use of the syringe. If needle 3 is retracted completely back into needle chamber 9, needle tip 4 can be extracted from needle bore 19 so that needle 3 is no longer constrained by bore 19. Because of the offset bias, needle 3 will realign itself away from the longitudinal axis of bore 19 so that needle tip 4 moves away from alignment with needle bore 19 and is caught within needle chamber 9 behind shoulder 22. If there is an attempt to extend needle 3 again, needle tip 4 will engage shoulder 22 preventing extension of needle 3. Attempts to force needle 3 forward may lead to needle tip 4 being at least partially imbedded in shoulder 22.

In an alternative arrangement, the longitudinal axis of needle bore 19 may be laterally offset from the longitudinal axis of stem 11. Needle 3 does not then need to be provided with an offset bias because the offset position of needle bore 19 will deflect needle 3 when supported therein. The resultant spring tension in needle 3 will ensure that realignment occurs when needle 3 is extracted from needle bore 19.

A further safety means may be provided to prevent or make it difficult for someone using the syringe to intentionally leave out a small portion of needle 3 after injection enabling re-use of the syringe. To provide this safety means, main body portion 6 may include an override chamber 24 at the terminal end of main body portion 6. Override chamber 24 may be cylindrical, may be in communication with and have a wider diameter than cylindrical chamber 7 and may have a longitudinal axis aligned with the longitudinal axis of main cylindrical chamber 7. A substantially annular shoulder or wall 25 may therefore be provided between cylindrical chamber 7 and override chamber 24. The terminal end of housing 1 may be sealed by an end cap 28 thereby closing off the open end of override chamber 24.

Diaphragm 26 may abut or be adjacent to annular shoulder 25 to partition and seal override chamber 24 from cylindrical chamber 7. In one arrangement, diaphragm 26 may have an interference fit within override chamber 24 in the position as shown in the illustrated embodiments. Frictional forces between the periphery of diaphragm 26 and the wall of override chamber 24 hold diaphragm 26 in position. It is also envisaged that a shallow undercut (not shown) be provided in the wall of override chamber 24 adjacent annular shoulder 25 to accommodate the periphery of diaphragm 26 so as to assist in locating and holding diaphragm 26 therein. Alternatively, diaphragm 26 may be supported by a resilient means which presses diaphragm 26 against annular shoulder 25. The resilient means may for example be a spring although other resilient means are also envisaged.

Piston 12 may have a peripheral wall 27 in sealing engagement with the wall of cylindrical chamber 7 when the syringe is in use. Peripheral wall 27 may be chamfered to provide a frusto-conical wall surface. The diameter of piston 12 preferably increases towards piston face 18. At least peripheral wall 27 of piston 12 is preferably resilient so that piston 12 is compressed when supported within cylindrical chamber 7 to maintain sealing engagement therein. Alternatively, peripheral wall 27 may have an annular groove for accommodating a separate sealing means such as an O-ring to maintain piston 12 in sealing engagement with cylindrical chamber 7.

Prior to use of the syringe with needle tip 4 initially supported in needle bore 19, piston 12 is located immediately adjacent to or abuts diaphragm 26 as shown in FIG. 1A. In the arrangement where diaphragm 26 is supported by resilient means, it is envisaged that piston 12 can at least partially depress diaphragm 26 into override chamber 24. As needle 3 is extended, piston 12 moves up cylindrical chamber 7 to the position shown in FIGS. 2A and B.

Figure 2C:
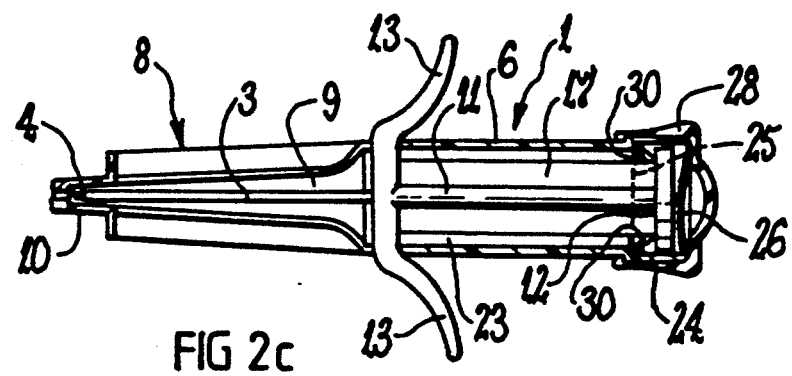
FIG. 2C is a longitudinal cross-sectional view of the hypodermic syringe of FIGS. 1A and 1B showing the needle fully retracted after completion of injection.

During the injection stroke, piston 12 moves back towards diaphragm 26. At the end of the injection stroke as shown in FIG. 2C, piston 12 presses and displaces diaphragm 26. To assist in dislodging diaphragm 26 when it is interference fitted within override chamber 24, a projection 29 may be provided on piston face 18. Projection 29 may extend at least substantially normal to and away from piston face 18 towards diaphragm 26, and may be located near or adjacent to the periphery of piston face 18. The pressing force provided by the retracting plunger assembly 2 is concentrated at the point where projection 29 engages diaphragm 26. This point is near the periphery of diaphragm 26 so that only a relatively small force is required to dislodge diaphragm 26 at its peripheral edge compared with the force that would be required if diaphragm 26 was pressed at its centre. The end of the injection can be clearly felt because of the drop in the resistance to the movement of handle members 13 felt by the user as diaphragm 26 is displaced. The displacement of diaphragm 26 results in the loss of compression within cylindrical chamber 7 disabling the syringe. Furthermore, as piston 12 enters override chamber 24, needle 3 may also be totally withdrawn from needle bore 19 into needle chamber 9 to trap needle 3 behind shoulder 22.

In certain situations, it is preferable for the syringe to be constructed so that it is difficult for the user to know when the end of the injection occurs. This prevents, for example, an intravenous drug user from controlling the use of the syringe so that needle 3 remains practically extended at the end of the injection thereby allowing re-use of the syringe by another person. In the arrangement described previously, where diaphragm 26 is supported by resilient means, it is difficult for the syringe user to know when piston 12 reaches this point. This is because diaphragm 26 can be readily displaced by piston 12 and there is no definite "stop" for plunger assembly 2 to show that the inoculant liquid has been fully injected by the syringe. It will therefore be difficult for the user to avoid the complete retraction of piston 12 beyond cylindrical chamber 7 and into override chamber 24 and the complete retraction of needle 3 within needle chamber 9.

Because the diameter of override chamber 24 is larger than cylindrical chamber 7, piston 12 can expand from its compressed state as it enters chamber extension 24. The chamfered peripheral wall 27 also assists in guiding piston 12 into override chamber 24. This is because as piston 12 reaches annular shoulder 25, the expansion of piston 12 and the shape of chamfered peripheral wall 27 of piston 12 acts to "pull" piston 12 into override chamber 24. This rearward pulling effect further ensures that it is difficult to prevent the full retraction of needle 3 after use of the syringe.

To further ensure that piston 12 remains trapped in override chamber 24, at least one projection or barb 30 may be provided on the face of the piston 12 directed towards needle 3 or may extend from each web 17 adjacent piston 12. Barbs 30 may be resilient and may extend substantially laterally and beyond peripheral wall 27 of piston 12 as shown in FIG. 1C when piston 12 is not constrained within cylindrical chamber 7. As shown in FIG. 1A, barbs 30 are initially deflected towards stem 11 when piston 12 is supported within cylindrical chamber 7. When piston 12 enters override chamber 24, barbs 30 expand laterally outwardly. Barbs 30 will engage annular wall 25 if there is an attempt to pull piston 12 back into cylindrical chamber 7.

The hypodermic syringe of FIGS. 1A to 3 may be used in the following manner:

(a) The syringe is supplied with needle 3 enclosed within safety shroud 8 to prevent contact and therefore contamination of needle 3.

(b) Needle cap 5 is twisted off to expose needle tip 4. For example, about 6 mm of needle 3 is exposed for the purposes of drawing inoculant liquid. The removal of needle cap 5 also provides an indication that the syringe has been used or tampered with.

(c) An inoculant liquid is drawn into liquid holding space 23 by moving handle members 13 towards forward tip 10 thereby exposing needle 3, to its full working length in readiness for injection. Having drawn in sufficient liquid, piston 12 may be activated into compression to remove any air in the normal manner.

(d) As the inoculation into the patient is proceeding, safety shroud 8 advances down needle 3 to a position where forward tip 10 touches the flesh at the conclusion of the injection movement. As diaphragm 26 must be displaced, a distinct resistance is felt at the conclusion of the injection delivery stroke so that the user is made aware that the dose has been administered.

(e) By continuing the compression stroke, the syringe is disabled as the above noted resistance is felt and the syringe is rendered useless and safe. Needle 3 is totally withdrawn within safety shroud 8 and compression in cylindrical chamber 7 is lost. In this way there is no way of touching needle 3 because it is shrouded as it leaves the patient's flesh.

A second preferred embodiment of the present invention is shown in FIGS. 4A and 4B. This embodiment is adapted for use in deep muscular inoculation but is otherwise identical to the first embodiment.

In the first embodiment needle 3 is progressively withdrawn into housing 1 during inoculation so that only needle tip 4 remains exposed at the end of the inoculation and just prior to needle 3 being fully withdrawn into housing 1 by the safety means described above. It is therefore not suitable for deep muscle inoculation where the syringe must penetrate deeply through a fat layer into the muscle. To adapt the present invention to this application, the second embodiment provides an elongate needle cap 105 to allow a greater length of needle 103 to be initially exposed when needle cap 105 is removed. Needle cap 105 may alsoo have twist tabs 1120 and may be integrally formed with safety shroud 108 with a frangible area in the form of an annular groove 121 in the wall of safety shroud 108 as in the first embodiment.

Needle 103 can therefore penetrate more deeply as a greater length remains exposed at the end of the innoculation and prior to full retraction of needle 103. Because needle 103 would be relatively longer than needle 3 of the first embodiment, the main body portion 106 would also need to be longer than main body portion 6 of the first embodiment to enable the longer needle 103 to be accommodated within housing 101. In particular, the override chamber (not shown) of main body portion 106 would need to be long enough to allow plunger assembly 102 to be fully retracted. To facilitate the use of this embodiment of the syringe, handle members 113 may be elongated in the longitudinal direction towards end cap 128 to enable the fingers to readily reach handle members 113.

Housing 1, 101 may be produced in two sections to facilitate the insertion of plunger assembly 2, 102 and needle 3, 103 therein. For example the safety shroud 8, 108 may be produced separately from the main body portion 6, 106. Plunger assembly 2, 102 may then be inserted into main body portion 6, 106 before safety shroud 8, 108 is secured thereon to form the complete housing 1, 101. Diaphragm 26 and any resilient means may be inserted through the open end of override chamber 24. End cap 28, 128 may then retain the above components therein.

In an alternative arrangement, housing 1, 101 could be produced as an integral unit with plunger assembly 2, 102 inserted into housing 1 through side slot 15, 115 in safety shroud 8, 108 or through the open end of main body portion 6, 106.

The various components of the syringe can be readily manufactured using conventional injection moulding methods and can be typically made of plastic materials. For example, the main body portion 6, 106 and safety shroud portion 8, 108 can be moulded from high impact polystyrene, piston assembly 2, 102 and end cap 28, 128 can be moulded from polypropelene and diaphragm 26 moulded from ABS.

The syringe of the present invention may be supplied within a container to prevent premature actuation of the safety means of the syringe. As previously noted, it is also envisaged that the syringe be supplied preloaded with a dose of inoculant liquid. As the needle will already be extended to its full working length from the syringe housing, an elongate needle cap is required to accommodate the extended needle. The syringe would be otherwise identical to the above described embodiments.

The hypodermic syringe of the present invention is much more safer to use and to dispose of because the needle is totally withdrawn into the housing at the end of the injection stroke of the syringe. There is no need to subsequently actuate a needle retracting means after the injection stroke eliminating the possibility of the needle remaining exposed after syringe use. Furthermore, the hypodermic syringe of the present invention can preferably only be used once thereby ensuring that a contaminated syringe cannot be re-used.

It should be appreciated that various modifications and additions may be made to the hypodermic syringe without departing from the ambit of the invention defined in the claims appended hereto.

I claim:

1. A hypodermic syringe including an elongate housing having rear and forward ends and a piston chamber therein, a plunger assembly having a piston, the piston chamber slidably supporting the piston to define an inoculant fluid storage space within the housing, a hollow needle supported by the plunger assembly and in communication with the storage space, the needle being extendable from the forward end of the housing and retractable into the housing during an injection stroke of the syringe wherein safety means are provided for preventing re-use of the syringe after the completion of the injection stroke, wherein the safety means includes an override chamber at the rear end of the housing adjoining the piston chamber and having a greater width than the piston chamber, and a displaceable diaphragm located at or adjacent the juncture of the piston and override chambers to partition and seal the override chamber from the piston chamber, the diaphragm being displaced by the piston as the piston enters the override chamber at the end of the injection stroke.

2. A hypodermic syringe including an elongate housing having a main body portion and a safety shroud portion adjoining the main body portion, a piston chamber provided within the main body portion, a plunger assembly having a piston, the piston chamber slidably supporting the piston to define an inoculant fluid storage space within the main body portion, a hollow needle supported by the plunger assembly and in communication with the storage space, the safety shroud portion having a forward tip and a needle chamber therein for accommodating the needle, a needle bore passing through the forward tip of the safety shroud portion from the needle chamber through which the needle can extend, the needle retracting into the safety shroud during an injection stroke of the syringe, wherein safety means are provided for preventing re-use of the syringe after the completion of the injection stroke, wherein the safety means includes an override chamber at the rear end of the main body portion adjoining the piston chamber and having a greater width than the piston chamber, and a displaceable diaphragm located at or adjacent the juncture of the piston and override chambers to partition and seal the override chamber from the piston chamber, the diaphragm being displaced by the piston as the piston enters the override chamber at the end of the injection stroke, the safety means further including a shoulder provided adjacent the needle bore within the needle chamber for trapping the tip of the needle when the needle is completely withdrawn from the needle bore into the needle chamber, the needle moving out of alignment with the needle bore when not constrained therein.

3. A hypodermic syringe according to claim 1 or 2 wherein the diaphragm has an interference fit within the override chamber, and a shallow undercut is provided in the wall of the override chamber to assist in locating and holding the diaphragm in position.

4. A hypodermic syringe according to claim 3 wherein the piston has a projection extending therefrom and towards the diaphragm, the projection being located adjacent to or near the periphery of the piston and being used to facilitate the dislodgment of the diaphragm.

5. A hypodermic syringe according to claim 3 wherein at least one outwardly extending barb is provided on the plunger assembly adjacent the piston for preventing movement of the piston back into the cylindrical chamber after the piston enters the override chamber.

6. A hypodermic syringe according to the claim 1 further including an elongate safety shroud portion adjoining the main body section and having a forward tip and a needle chamber therein for accommodating the needle, and a needle bore passing through the forward tip of the safety shroud portion from the needle chamber, through which the needle extends.

7. A hypodermic syringe according to claim 6 wherein the safety means further includes a shoulder provided adjacent the needle bore and within the needle chamber for trapping the tip of the needle when the needle is completely withdrawn from the needle bore into the needle chamber, the needle moving out of alignment with the needle bore when not constrained therein.

8. A hypodermic syringe according to claim 6 or 2 wherein a needle cap is integrally formed with and separable from the forward tip of the safety shroud portion, the forward tip having a frangible weakened portion adjacent to the needle cap whereby the needle cap can be twisted and separated from the forward tip to expose the portion of the needle held therein.

9. A hypodermic needle according to claim 6 or 2 wherein the plunger assembly includes an elongate stem having the piston at one end thereof, and at least one handle member extending laterally from the stem at or adjacent the opposing end thereof.

10. A hypodermic syringe according to claim 9 wherein at least one elongate longitudinal slot is provided in the housing to allow the or each handle member to extend out from the housing.

11. A hypodermic syringe according to claim 10 wherein a peripheral wall extends along at least a substantial portion of the periphery of the or each longitudinal slot.

12. A hypodermic needle according to claim 9 wherein the needle communicates with the inoculant fluid storage space by way of a passage passing through the plunger assembly.

* * * * *